US006883222B2

(12) United States Patent
Landau

(10) Patent No.: US 6,883,222 B2
(45) Date of Patent: Apr. 26, 2005

(54) DRUG CARTRIDGE ASSEMBLY AND METHOD OF MANUFACTURE

(75) Inventor: Sergio Landau, Laguna Niguel, CA (US)

(73) Assignee: Bioject Inc., Tualatin, OR (US)

(*) Notice: Subject to any disclaimer, the term of this patent is extended or adjusted under 35 U.S.C. 154(b) by 22 days.

(21) Appl. No.: 10/272,689

(22) Filed: Oct. 16, 2002

(65) Prior Publication Data

US 2004/0074076 A1 Apr. 22, 2004

(51) Int. Cl.$^7$ .............................................. B23P 21/00
(52) U.S. Cl. .......................... 29/469; 53/426; 53/432; 604/403
(58) Field of Search .......................... 29/428, 429, 458, 29/469; 53/425, 426, 432, 511; 604/403

(56) References Cited

U.S. PATENT DOCUMENTS

| | | |
|---|---|---|
| 3,057,349 A | 10/1962 | Ismach |
| 3,115,133 A | 12/1963 | Morando |
| 3,202,151 A | 8/1965 | Kath |
| 3,292,621 A | 12/1966 | Banker |
| 3,425,413 A | 2/1969 | Stephens |
| 3,507,276 A | 4/1970 | Burgess |
| 3,561,443 A | 2/1971 | Banker |
| 3,688,765 A | 9/1972 | Gasaway |
| 3,714,943 A | 2/1973 | Yanof et al. |
| 3,788,315 A | 1/1974 | Laurens |
| 3,908,651 A | 9/1975 | Fudge |
| 3,945,379 A | 3/1976 | Pritz et al. |
| 4,124,024 A | 11/1978 | Schwebel et al. |
| 4,266,541 A | 5/1981 | Landau |
| 4,342,310 A | 8/1982 | Lindmayer et al. |
| D277,506 S | 2/1985 | Ibis |
| 4,592,742 A | 6/1986 | Landau |
| 4,596,556 A | 6/1986 | Morrow et al. |

(Continued)

FOREIGN PATENT DOCUMENTS

| | | |
|---|---|---|
| WO | WO98/52632 | 11/1998 |
| WO | WO00/33899 | 6/2000 |
| WO | WO00/48654 | 8/2000 |
| WO | WO01/74425 | 10/2001 |

*Primary Examiner*—David P. Bryant
*Assistant Examiner*—Stephen Kenny
(74) *Attorney, Agent, or Firm*—Kolisch Hartwell, P.C.

(57) ABSTRACT

A method of manufacture for a drug cartridge assembly. The method includes providing a drug cartridge, providing a nozzle sub-assembly, and sterilizing the drug cartridge and nozzle sub-assembly. The method further includes assembling the drug cartridge and nozzle sub-assembly together in a configuration that enables ejection of liquid out of the drug cartridge through the nozzle sub-assembly. The method further includes filling the drug cartridge with a liquid, such as an injectable drug. The method may include separate sterilization of the drug cartridge and nozzle sub-assembly, using different sterilization processes. Portions of the method may be performed prior to sterilization within a first cleanroom, with subsequent steps being performed in a second cleanroom having a substantially lower particulate-per-volume rating than the first cleanroom.

14 Claims, 2 Drawing Sheets

U.S. PATENT DOCUMENTS

| | | | |
|---|---|---|---|
| 4,623,332 A | 11/1986 | Lindmayer et al. | |
| 4,680,027 A | 7/1987 | Parsons et al. | |
| 4,717,384 A | 1/1988 | Waldeisen | |
| 4,790,824 A | 12/1988 | Morrow et al. | |
| 4,940,460 A | 7/1990 | Casey et al. | |
| 4,941,880 A | 7/1990 | Burns | |
| 4,966,581 A | 10/1990 | Landau | |
| 5,009,637 A | 4/1991 | Newman et al. | |
| 5,009,654 A * | 4/1991 | Minshall et al. | 604/410 |
| 5,024,656 A | 6/1991 | Gasaway et al. | |
| 5,049,125 A | 9/1991 | Accaries et al. | |
| 5,064,413 A | 11/1991 | McKinnon et al. | |
| 5,312,335 A | 5/1994 | McKinnon et al. | |
| D349,958 S | 8/1994 | Hollis et al. | |
| 5,334,144 A | 8/1994 | Alchas et al. | |
| 5,383,851 A | 1/1995 | McKinnon, Jr. et al. | |
| 5,399,163 A | 3/1995 | Peterson et al. | |
| 5,503,627 A | 4/1996 | McKinnon et al. | |
| 5,505,697 A | 4/1996 | McKinnon, Jr. et al. | |
| 5,520,639 A | 5/1996 | Peterson et al. | |
| 5,554,125 A * | 9/1996 | Reynolds | 604/187 |
| 5,597,530 A * | 1/1997 | Smith et al. | 422/28 |
| 5,879,327 A | 3/1999 | DeFarges et al. | |
| 5,891,086 A | 4/1999 | Weston | |
| 5,899,880 A | 5/1999 | Bellhouse | |
| 5,993,412 A | 11/1999 | Deily et al. | |
| 6,004,287 A | 12/1999 | Loomis et al. | |
| 6,065,270 A * | 5/2000 | Reinhard et al. | 53/426 |
| 6,096,002 A | 8/2000 | Landau | |
| 6,132,395 A | 10/2000 | Landau et al. | |
| 6,210,359 B1 | 4/2001 | Patel et al. | |
| 6,224,567 B1 | 5/2001 | Roser | |
| 6,231,540 B1 | 5/2001 | Smedegaard | |
| 6,263,641 B1 * | 7/2001 | Odell et al. | 53/425 |
| 6,264,629 B1 | 7/2001 | Landau | |
| 6,383,168 B1 | 5/2002 | Landau et al. | |

\* cited by examiner

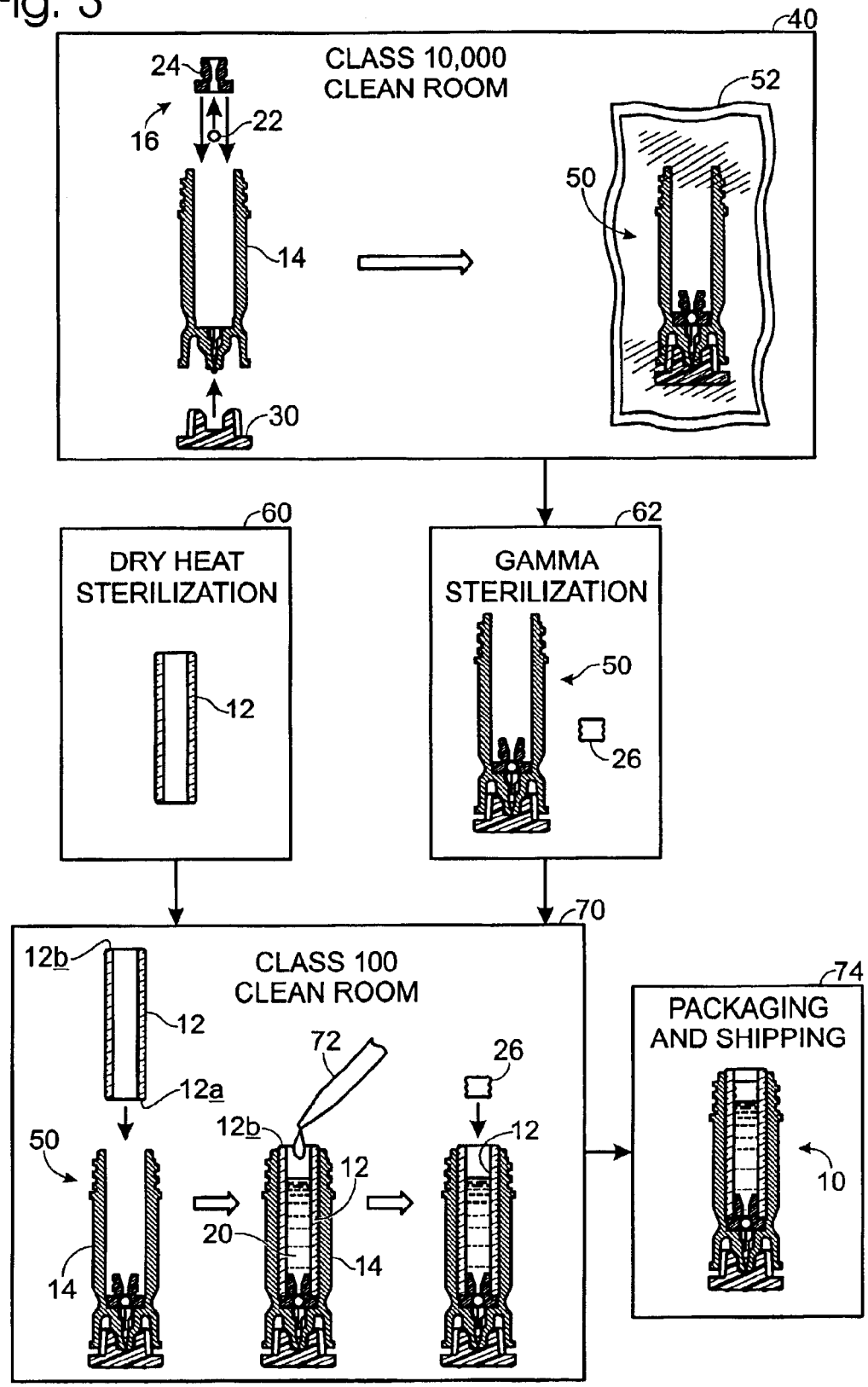

DRUG CARTRIDGE ASSEMBLY AND METHOD OF MANUFACTURE

BACKGROUND OF THE INVENTION

The invention relates to a method of manufacture for a drug cartridge assembly configured for use in providing an injection.

Drug cartridge assemblies and other injection devices commonly include a number of different components. Typically, several of the components are fabricated from plastic, because plastic is durable and relatively inexpensive. Plastic, however, normally is not the material of choice for the container that holds the drug. Certain elements present in plastics may interact with certain drugs, for example, or may leach into and contaminate the drug. Accordingly, the liquid drug is often held within a container, such as a vial or cylindrical cartridge, which is made from medical grade borosilicate glass.

Drug cartridge assemblies must be relatively free of contamination. Sterilization and cleaning of components are therefore important considerations in any process used to manufacture a drug cartridge assembly. Many existing manufacturing methods employ cleaning and sterilization techniques that are ill-suited for use in preparing drug cartridge assemblies, or other sterile devices constructed from multiple components. In particular, existing manufacturing methods often employ sterilization processes that, while appropriate for some components, are ineffective or harmful when used on other components. In addition, existing manufacturing methods often do not efficiently utilize cleanroom environments, and thereby add unnecessarily to manufacturing costs.

SUMMARY OF THE INVENTION

The present invention provides a method of manufacture for a sterile device such as a drug cartridge assembly. The method includes providing a drug cartridge, providing a nozzle sub-assembly, and sterilizing the drug cartridge and nozzle sub-assembly. The method further includes assembling the drug cartridge and nozzle sub-assembly together in a configuration that enables ejection of liquid out of the drug cartridge through the nozzle sub-assembly. The method also includes filling the drug cartridge with a liquid, such as an injectable drug. Sterilization of the drug cartridge and nozzle sub-assembly may be performed separately, using different types of sterilization processes. Also, part of the method may be performed prior to sterilization within a first cleanroom, with subsequent steps being performed in a second cleanroom, where the second cleanroom has a substantially lower particulate-per-volume rating than the first cleanroom.

BRIEF DESCRIPTION OF THE DRAWINGS

FIG. 3 is a schematic view depicting exemplary methods that may be used to assemble the drug cartridge assembly of FIGS. 1 and 2, and prepare it for use in providing an injection.

DETAILED DESCRIPTION OF THE PREFERRED EMBODIMENT(S)

The following description will address various implementations of a method of manufacture for a sterile device. The methods are widely applicable, though they are particularly advantageous where the device is to be constructed from multiple components or from more than one type of material, where certain sterilization processes pose problems relating to only a portion of the device, and/or where it is important that certain steps be carried out in cleanroom-type environment. The methods described herein may, for example, be advantageously employed to prepare a variety of drug cartridge assemblies and other sterile medical devices.

For purposes of illustration only, the exemplary methods described herein will be discussed primarily in the context of a drug cartridge assembly. Further discussion and examples of drug cartridges and cartridge assemblies may be found in U.S. Pat. No. 6,132,395, by Sergio Landau and James M. Bonicatto, entitled "Needleless Syringe With Prefilled Cartridge," which issued on Oct. 17, 2000, and U.S. Pat. No. 6,383,168, by Sergio Landau and James M. Bonicatto, entitled "Needleless Syringe with Prefilled Cartridge," which issued on May 7, 2002, the disclosures of which are incorporated herein by this reference, in their entireties and for all purposes.

Figure 2:
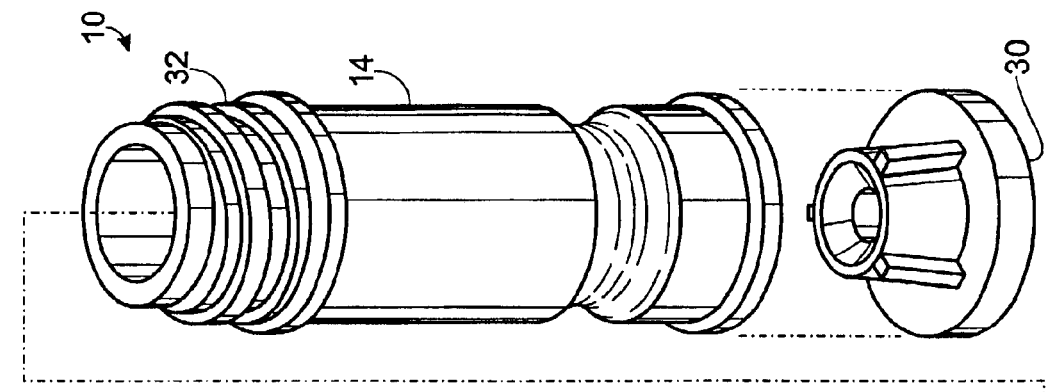
FIG. 2 is an exploded view of the drug cartridge assembly of FIG. 1.
Figure 1:
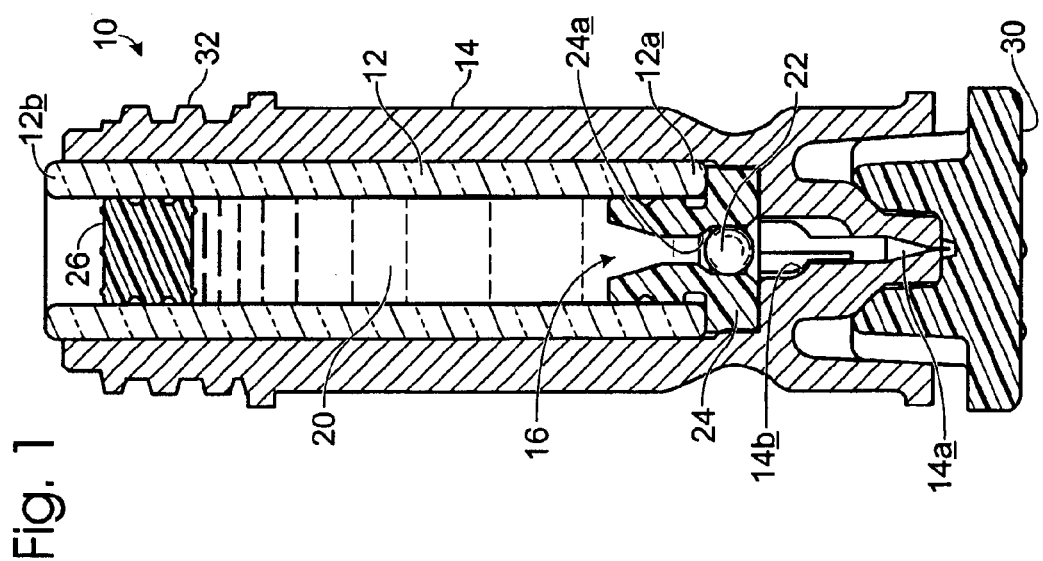
FIG. 1 is a sectional view of a drug cartridge assembly.

FIGS. 1 and 2, respectively, depict a sectional view and an exploded view of a drug cartridge assembly 10. As shown, drug cartridge assembly 10 typically includes a liquid container, such as drug cartridge 12, and a nozzle 14. In the depicted example, nozzle 14 also serves as a housing for cartridge 12, as shown in FIG. 1, although a housing may be provided separately from nozzle 14, or may be omitted altogether. The depicted exemplary cartridge is formed as an open-ended cylinder, though other shapes and configurations may be employed, as desired.

A cartridge seal 16 may be provided at end 12a of cartridge 12, to maintain liquid 20 (e.g., a dose of drug) within cartridge 12 until it is to be ejected from drug cartridge assembly 10. Cartridge seal 16 may be implemented in a variety of ways, in order to maintain liquid 20 within cartridge 12 until the user desires to eject the liquid, for example, to administer an injection. As shown, cartridge seal 16 may be implemented as a ball-type check valve, including a ball 22 and a sealing member 24. Sealing member 24 may be secured with end 12a of cartridge 12, and includes a seat 24a. When ball 22 engages seat 24a, the end of the cartridge is sealed. A spring or other biasing member (not shown) may be provided to urge ball 22 upward into sealing engagement with seat 24a. Typically, a plunger 26 or like structure is provided to seal opposing end 12b of cartridge 12. As shown in FIG. 1, liquid 20 may thus be sealed within drug cartridge 12 by cartridge seal 16 and plunger 26.

Nozzle 14 typically includes an opening 14a through which liquid 20 from cartridge 12 may be ejected. Opening 14a may have any practicable dimensions, though it typically is narrower than the interior of cartridge 12. Use of a relatively narrow opening may facilitate high-pressure ejection of liquid 20, and enable injection of the liquid into a well-defined injection site. The end of nozzle 14 may be fitted with a removable cap 30 when drug cartridge assembly 10 is not being used, for example during shipping or storage.

As discussed above, nozzle 14 typically houses drug cartridge 12, though it will be appreciated that the nozzle 14 may take alternate forms. For example, nozzle 14 may be formed as a structure which is positioned on, or connected to, end 12a of cartridge 12, without wrapping around or otherwise enclosing the body of the cartridge. Also, though cartridge seal 16 is a separate component in the depicted example, it should be appreciated that the seal may be formed integrally with nozzle 14 and/or cartridge 12.

The various components of drug cartridge assembly 10 may be made from a variety of different materials, including metals, plastics and other polymeric materials, ceramics, etc. Typically, in the depicted exemplary device, nozzle 14, cap 30, ball 22 and sealing member 24 are fabricated from plastic, or from another polymeric material. Additionally, it will often be desirable to form sealing member 24 and/or ball 22 from an elastic, resilient material, such as rubber, in order to facilitate effective sealing. Typically, use of polymeric materials as described above provides for cost-efficient manufacture and a durable device.

Though many components of drug cartridge assembly 10 can be advantageously formed from plastic, it will in many cases be preferable to manufacture drug cartridge 12 from glass, instead of from plastic or other materials. Use of thermoplastic containers, for example, may involve risks of interaction between the drug and the container. The drug may chemically react with the plastic, or may cause materials in the plastic to leach into the drug, thereby introducing impurities in the drug. In periods of extended storage, such exposure to a plastic container may result in degradation of the drug. In certain applications, glass may also be easier to clean and sterilize during initial preparation, and/or when being recycled for subsequent additional uses. It should be appreciated, however, that drug cartridge 12 may nonetheless be made from plastic or other materials other than glass.

It will often be desirable to provide drug cartridge assembly 10 to the end user as a pre-filled, ready-to-use assembly that has already been sterilized. The user would then simply need to remove cap 30 and operatively engage drug cartridge assembly 10 with an injection device (not shown), and then an injection could be administered. As shown in FIG. 2, threads 32 or another attachment mechanism may be provided to facilitate engagement of drug cartridge assembly 10 with an injection device. Typically, threads 32 are positioned on the outer surface of nozzle 14 opposite nozzle opening 14a.

An injection may be administered by forcing plunger 26 toward nozzle opening 14a (i.e., downward in FIG. 1) to apply pressure to liquid 20. Plunger 26 may be forced downward via movement of a plunger rod (not shown) or other structure brought into contact with plunger 26, through application of fluid pressure to plunger 26, or through other appropriate methods and structures. Upon application of sufficient pressure to the liquid supply, ball 22 is forced out of engagement with seat 24a and downward into a cavity 14b formed near the forward end of nozzle 14. When ball 22 is in this advanced state, liquid 20 from drug cartridge 12 can flow within cavity 14b around ball 22 and out through nozzle opening 14a.

When drug cartridge assembly 10 is provided in the ready-to-use configuration described above and shown in FIG. 1, the end user does not have to fill the injection device with a measured dose of injectable liquid, as is required with many existing injection devices. Filling adds an extra step, and can increase the risk of contaminating the liquid dose with air bubbles or other contaminants. Filling can also lead to spilling of the drug, and increases the risk that the user will come into undesired contact with the drug. In addition, a sterile adapter fitting is often required to couple the liquid container of the injection device with a source of injectable liquid. Accordingly, in most cases it will be desirable to implement drug cartridge assembly 10 in a pre-filled, ready-to-use state, as described.

FIG. 3 schematically depicts an exemplary method which may be used to prepare drug cartridge assembly 10. As will be explained, the method may include various assembly steps, it may be siliconized, and may be subjected to washing and other sterilization processes prior to packaging for shipment.

In many cases, it will be desirable to implement some or all of the method in a cleanroom or other controlled setting where airborne contamination is reduced from normal levels. For example, some preparation steps may be performed within cleanroom 40, which, as shown, may be a class 10,000 cleanroom. Specifically, as shown in FIG. 3, cartridge seal 16 may be assembled within cleanroom 40 by inserting ball 22 into sealing member 24. Cartridge seal 16 is then positioned within the interior of nozzle 14, so that it generally covers nozzle opening 14a in a position that enables the cartridge seal to seal between open cartridge end 12a and nozzle opening 14. Cap 30 may also be secured in place on the end of nozzle 14. The assembled components are designated at 50, and may be referred to collectively as the nozzle sub-assembly. Although the depicted nozzle sub-assembly is fabricated from a number of separate components, it should be understood that nozzle sub-assembly may be formed as a single unitary piece.

The term "cleanroom" as used herein should not be limited to an entire room, but might alternatively be a clean area, such as that defined under a laminar flow hood.

While nozzle sub-assembly 50 is still within cleanroom 40, nozzle sub-assembly 50 may be packed within a sterile container, such as double bag 52. As discussed below, the depicted exemplary method also includes radiation-based sterilization of nozzle sub-assembly 50. Accordingly, it will typically be preferred that the double bag 52 or other container used for nozzle sub-assembly 50 be suitable for exposure to radiation. Alternatively, nozzle sub-assembly 50 may be removed from the initial packaging prior to radiation sterilization. It will often be preferable, however, to maintain nozzle sub-assembly 50 within the sterile packaging until final assembly of the nozzle sub-assembly with other components of drug cartridge assembly 10 (discussed below).

As discussed above, the components of drug cartridge assembly 10 may be fabricated from different materials. Sterilization and cleaning techniques that are suitable for one type of material may not be appropriate for another. Also, the particular way a component is used may affect what methods of cleaning and sterilization are most advantageous. Drug cartridge 12, for example, typically comes into direct contact with liquid (e.g., with a dose of an injectable drug). Accordingly, it will typically be desirable to wash and rinse drug cartridge 12 at some point during the preparation of cartridge assembly 10. Washing normally is performed during initial manufacture, and between uses where drug cartridge 12 is recycled for multiple uses. Although it is typical to wash cartridge 12, washing may not be appropriate or necessary for nozzle 14, or for the other components of drug cartridge assembly 10.

Similarly, radiation-based sterilization may not be suitable for all of the components of drug cartridge assembly 10. As discussed above, certain advantages may be had by fabricating drug cartridge 12 from glass, and the drug cartridge typically will be fabricated from that material. However, gamma radiation often will produce an orange or brown discoloration when used to sterilize glass. This can be undesirable, particularly where it is important that it be easy to view the contents of drug cartridge 12. Thermal sterilization may also present certain problems, and typically is not preferred as a primary method for sterilizing medical devices made from plastic and other polymeric materials. Heat, for example, can melt components and/or cause other damage.

Accordingly, the method of preparing drug cartridge assembly 10 for use may include separate sterilization processes for different components. As shown in FIG. 3, a thermal sterilization process, such as dry heat sterilization process 60, may be employed to sterilize drug cartridge 12. Washing and/or rinsing of the cartridge may be performed before, during or after the thermal sterilization. Typically, a separate radiation-based process, such as gamma sterilization 62, is employed to sterilize nozzle sub-assembly 50 and plunger 26.

It is also typical to siliconize drug cartridge 12 prior to assembly. This is typically done by treating with 1% silicon emulsion, and then baking in a lehr until the glass temperature reaches 300 degrees Celsius for a period of 25 minutes+/−5 minutes.

After sterilization occurring at 60 and 62, additional assembly and preparation may be performed within another cleanroom 70. Cleanroom 70 typically is used for final processing, and will therefore normally have a substantially lower particulate-per-volume classification than cleanroom 40. In the depicted method, for example, cleanroom 70 has a particulate concentration rating which is 1,000 times lower than that of cleanroom 40. Separate cleanrooms may be employed, as in the depicted example, to minimize the amount of preparation occurring within the "cleaner" environments. Minimizing usage of the cleaner room saves on cost, as cleaner environments are often more expensive to use and maintain. However, it should be understood that not all implementations of the described method require use of cleanroom environments with differing classifications. The assembly steps shown in cleanroom 40, for example, may instead be performed within cleanroom 70, or vice versa.

Drug cartridge 12, nozzle sub-assembly 50 and plunger 26 may be placed within cleanroom 70, typically after sterilization has been performed. Preparation within cleanroom 70 typically includes inserting drug cartridge 12 into nozzle 14, as indicated on the left side of cleanroom 70. The cartridge is positioned so that end 12a is firmly engaged with cartridge seal 16, as shown in FIG. 1. At this point, cartridge end 12b is open and may receive liquid, as shown in the center of cleanroom 70. Specifically, a quantity of liquid 20 (e.g., a metered does of an injectable drug) is dispensed from liquid supply 72 into cartridge 12. Plunger 26 may then be inserted into the open end of cartridge 12 to seal the liquid dose within the cartridge.

As shown at 74, drug cartridge assembly 10 may be further processed, for example, to prepare the product for shipping. Though reference number 74 denotes a process representation that is positioned outside of cleanroom 70, it should be appreciated that final processing tasks will often occur at least partly within cleanroom 70. The fully assembled drug cartridge assembly may, for example, be placed within a sterile bag while within cleanroom 70, with additional final preparation such as packaging, labeling, etc. being performed outside of the cleanroom. Alternatively, final preparation may occur completely within or outside of cleanroom 70.

It should be understood that the described method may be implemented in a wide variety of ways.

For example, although FIG. 3 depicts only a single drug cartridge assembly, the described method often will be implemented on a larger scale to efficiently mass-produce drug cartridge assemblies in large numbers. According to one such implementation, plural cartridges 12 are disposed on a tray or like holding device, and remain on the tray during at least part of the manufacturing process. While on the tray, for example, the cartridges may be washed, depyrogenized, and subjected to other cleaning/sterilization processes (e.g., dry heat sterilization process 60). Such a tray may also be used to facilitate the other processes described above, such as the steps performed within cleanroom 70.

It should also be understood that the various steps described above may be performed in any practicable order. The process arrows shown in FIG. 3 are intended only to illustrate a particular example, and should not be interpreted as requiring steps to be performed in a particular sequence. Cartridge 12 may, for example, be filled and sealed prior to positioning of the cartridge within nozzle 14. Gamma sterilization 62 may be performed prior to any assembly of the components to be irradiated. Such radiation is normally performed at a level of from 26 to 40 Krads, and is typically at between 32 and 34 Krads. Many other variations are possible.

Those skilled in the relevant arts will also appreciate that the methods described herein are generally applicable to sterile devices having multiple components or parts. As discussed above, individual components or groups of components are separated based on the suitability of available sterilization techniques. In the above illustration, for example, glass components are separated from components made from plastic and other polymeric materials. The separated components are then sterilized separately using the appropriate sterilization method. Glass, for example, is thermally sterilized, and the polymeric components are sterilized via radiation.

The components are then assembled together to produce the final assembled device. Typically, this final step is conducted in a cleanroom with a relatively low particulate-per-volume classification. For many sterile devices, there will be a number of components that are made from the same material, and/or that may be sterilized using the same method. In such a case, it will often be appropriate to assemble these components together prior to sterilization. For example, in the above illustration, nozzle sub-assembly 50 is assembled from its component parts prior to gamma sterilization. Such pre-sterilization assembly will often be conducted within a cleanroom. Because of the subsequent sterilization, the cleanroom used for the pre-sterilization assembly may not need to have a particularly low particulate-per-volume rating. Indeed, in practice, the pre-sterilization cleanroom will often have a rating that is substantially higher (i.e., a "less clean" environment) than that of the cleanroom used for final assembly, in order to make cost-efficient use of cleanroom resources.

While the present invention has been particularly shown and described with reference to the foregoing preferred embodiments and implementations, those skilled in the art will understand that many variations may be made therein without departing from the spirit and scope of the invention as defined in the following claims. The description of the invention should be understood to include all novel and non-obvious combinations of elements described herein, and claims may be presented in this or a later application to any novel and non-obvious combination of these elements. Where the claims recite "a" or "a first" element or the equivalent thereof, such claims should be understood to include incorporation of one or more such elements, neither requiring nor excluding two or more such elements.

What is claimed is:

1. A method of preparing a sterile drug cartridge assembly, comprising:
   providing a drug cartridge;
   providing a nozzle sub-assembly, where the drug cartridge and nozzle-sub-assembly are adapted to be engaged together to enable ejection of liquid from the drug cartridge out through the nozzle sub-assembly;
   assembling the nozzle subassembly and otherwise preparing the nozzle sub-assembly for sterilization in a first cleanroom;
   sterilizing the nozzle sub-assembly;
   sterilizing the drug cartridge; and
   positioning the drug cartridge in a ready-to-use position within the nozzle sub-assembly, and filling and sealing the drug cartridge, where the positioning, filling and sealing are performed within a second cleanroom, the second cleanroom having a particulate-per-volume rating which is at least ten times lower than that of the first cleanroom.

2. The method of claim 1, where preparing the nozzle sub-assembly includes providing a nozzle having a nozzle opening to accommodate ejection of liquid, and positioning a sealing mechanism adjacent the nozzle opening so that the sealing mechanism covers the nozzle opening.

3. The method of claim 1, where sterilizing the nozzle sub-assembly is performed with a radiation-based sterilization process.

4. The method of claim 3, where sterilizing the nozzle sub-assembly is performed using gamma radiation.

5. The method of claim 3, where sterilizing the drug cartridge is performed with a thermal sterilization process, and is performed separately from sterilization of the nozzle sub-assembly.

6. The method of claim 1, where sterilization of the nozzle sub-assembly and drug cartridge are performed separately using different sterilization processes.

7. The method of claim 1, further comprising washing the drug cartridge.

8. The method of claim 1, further comprising depyrogenizing the drug cartridge.

9. The method of claim 1, further comprising siliconizing the drug cartridge.

10. The method of claim 1, where sealing the drug cartridge includes securing a valve structure between an opening in the nozzle sub-assembly and an opening in the drug cartridge.

11. The method of claim 10, where sealing the drug cartridge further includes disposing a plunger within another opening of the drug cartridge.

12. The method of claim 1, where the first cleanroom is a class 10,000 cleanroom and the second cleanroom is a class 100 cleanroom.

13. A method of manufacturing a medical device, comprising:
   separating a glass drug container of the medical device from another component of the medical device;
   sterilizing the glass drug container separately from the other component of the medical device, where the glass drug container is sterilized with a thermal-based sterilization process, and where the other component is sterilized using a radiation-based sterilization process;
   filling the glass drug container with a metered dose of an injectable drug;
   assembling the glass drug container with the other component of the medical device; and
   disposing the glass drug container and the other component of the medical device within a sterile package.

14. A method of manufacturing a sterile injection device, comprising:
   providing a liquid container;
   providing a nozzle sub-assembly, where the liquid container and nozzle-sub-assembly are adapted to be engaged together to enable ejection of liquid from the liquid container out through the nozzle sub-assembly;
   preparing the nozzle sub-assembly for sterilization, where such preparation is performed in a first cleanroom;
   sterilizing the nozzle sub-assembly via irradiation;
   sterilizing the liquid container separately from the nozzle sub-assembly using a thermal sterilization process; and
   securing the liquid container and nozzle sub-assembly together, and filling and sealing the liquid container, where the securing, filling and sealing are performed within a second cleanroom, the second cleanroom having a particulate-per-volume rating which is at least ten times lower than that of the first cleanroom.

* * * * *